United States Patent [19]

Fago et al.

[11] Patent Number: 4,668,229
[45] Date of Patent: May 26, 1987

[54] DISPOSABLE ABSORBENT DEVICE FOR POST-URINARY DRIP

[75] Inventors: Anthony Fago, Cleveland; Alfred D. Lobo, Cleveland Heights, both of Ohio

[73] Assignee: Alfred D. Lobo & Co., L.P.A., Cleveland, Ohio

[21] Appl. No.: 905,144

[22] Filed: Sep. 9, 1986

Related U.S. Application Data

[63] Continuation of Ser. No. 725,567, Apr. 22, 1985, abandoned.

[51] Int. Cl.$^4$ ............................................. A61M 1/00
[52] U.S. Cl. ..................................... 604/327; 604/349
[58] Field of Search ...................... 128/760, 762, 767; 604/318, 327, 349, 351, 353; 4/144.1–144.4

[56] References Cited

U.S. PATENT DOCUMENTS

| | | | |
|---|---|---|---|
| 2,445,220 | 7/1948 | Isaacson | 604/349 |
| 2,864,369 | 12/1958 | Morrow | 604/353 |
| 3,357,430 | 12/1967 | Rosenborg | 604/353 |
| 4,197,849 | 4/1980 | Bostick | 604/318 |
| 4,314,558 | 2/1982 | Koupman | 128/760 |
| 4,337,327 | 6/1982 | Stoy | 525/280 |
| 4,354,494 | 10/1982 | Hogin | 604/319 |

Primary Examiner—C. Fred Rosenbaum
Assistant Examiner—J. L. Kruter
Attorney, Agent, or Firm—Alfred D. Lobo

[57] ABSTRACT

The vexing problem of post-urinary drip in males can be solved by providing a loop means removably disposed around the scrotum, the loop means being located above the testicles. The loop means is attached to a slotted sheath of polymeric material which sheaths the penis in its normal or "rest" (non-erect) position; the loop and sheath may each be formed, integrally or separably, from an urine-absorbent ("u-a" for brevity) film of hydrophilic synthetic resinous material; or, the loop and sheath may each be formed from a natural fabric such as cotton, or a non-absorbent synthetic resinous material in which sheath a u-a liner means, preferably of polymeric material such as a monoolefinically unsaturated carboxylic acid-containing polymer is removably held. The hydrophilic polymer is formed from a block copolymer of sequences of acrylonitrile and sequences of a major portion of glutarimide units; or, a film formed from sequences of acrylonitrile and sequences of a major portion of acrylamide units. The sheath has a longitudinal slot in its upper surface through which the penis may be unsheathed for use without the sheath being removed from the base of the penis. After urination, the penis is resheathed by insertion through the slot.

3 Claims, 10 Drawing Figures

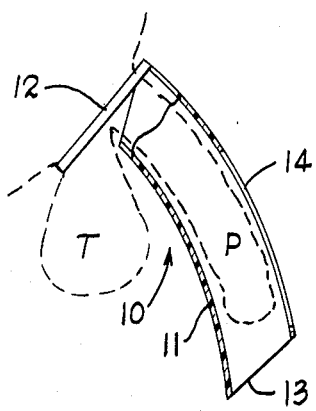
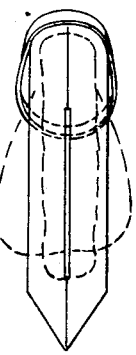
Fig. 1          Fig. 2
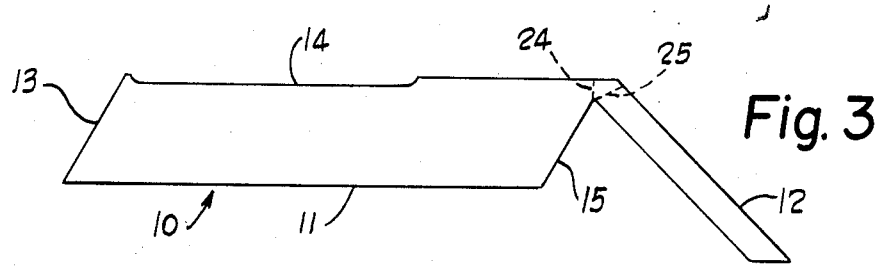
Fig. 3
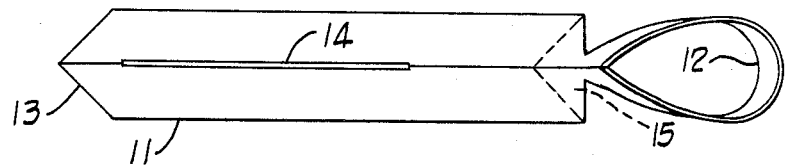
Fig. 4
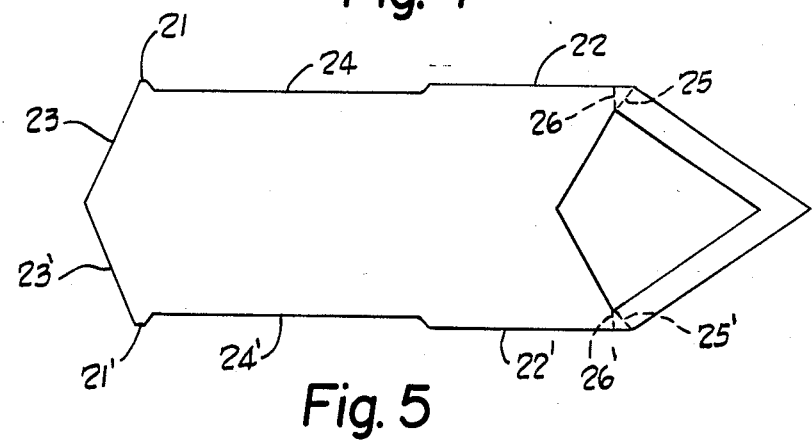
Fig. 5

DISPOSABLE ABSORBENT DEVICE FOR POST-URINARY DRIP

This is a continuation of application Ser. No. 725,567, filed Apr. 22, 1985 now abandoned.

BACKGROUND OF THE INVENTION

This invention relates to a novel and useful article which protects a male's clothing against being soiled by dripping urine such as is commonly referred to as post-urinary drip.

More specifically the article provides for a disposable sheath, optionally in combination with a liner means ("liner" for brevity), at least one of which is made of urine-absorbent ("u-a" for brevity) material which has a high absorbence for urine. The liner, if used, is placed in the sheath which sheaths the penis, and if desired, the sheath and liner may together be disposable, or the liner may be removed from the sheath and disposed of, while the sheath may be reused.

The article not only provides a cosmetic function in that it avoids unsightly stains caused by a posturinary drip, but it provides a hygenic function by avoiding skin contact with that portion of apparel, for example "shorts", "briefs" or other underpants which are wetted with the urine. Because a post-urinary drip can drippingly wet through underpants, the article will also save afflicted males from undue embarassment.

It should be appreciated that the article of this invention is wholly inadequate to cope with an incontinent male, or where nerve injury has occurred, as in certain neurological diseases, or where there is abnormal sphincter weakness. As will presently be evident from a detailed description of the article, it is particularly designed for absorbing a typical post-urinary drip such as is experienced by a mature male who is no longer a young adult. Such a drip, deemed attributable to a slight sphincter weakness or a prostate problem in the mature male, may range in volume from a few drops which together are about 0.1 ml, to a relatively large number of drops which together add up to about 10 ml, at some usually unpredictable time after a single normal urination.

As will also presently be evident, the article of this invention is not a condom or contraceptive, simply because its sheath is specifically designed as a relatively inextensible, non-resilient loose-fitting covering for the penis in its normal or "rest" position, that is, when there is no either partial or full erection such as is present during coitus, and it would not confine semen because the sheath has a slot in it. By non-resilient I mean that the sheath lacks the ability of a strained body, by virtue of its (the body's) high yield strength and low elastic modulus, to recover its size and form following deformation.

Though it is evident that any device for absorbing post-urinary drip must be worn externally, that is, next to the skin and exteriorly of the body, the problem is how to do so effectively. A solution was preferred more than a century ago in the United States of America in U.S. Pat. No. 87,932 to E. F. Hoffmann, and in Great Britain more than fifty years ago in GB Pat. Nos. 8,641 and 264,690, but these devices were uncomfortable and inconvenient to wear and lacked a highly absorbent material for use as a u-a pad.

A non-elastomeric and non-resilient sheath was disclosed as early as in the U.S. Pat. No. 87,932, but they chose to use a belt (for around the waist) and a testicle-supporting sack to support the sheath. Such belt-supported devices, however, are uncomfortable, and therefore still a problem. This problem of comfortably positioning a penis sheath to combat post-urinary drip has persisted for over a century. The formidable nature of the problem will better be appreciated when one duly notes that U.S. Pat. Nos. 3,958,574 and 4,064,888 elected simply to avoid the problem. By non-elastomeric I refer to the sheath's inability to be stretched under low stress at room temperature, to at least twice its original length, and upon immediate release of the stress, to return with force to its approximate original length.

SUMMARY OF THE INVENTION

It has been discovered that the vexing problem of post-urinary drip in males can be solved by providing a loop means removably disposed around the scrotum, the loop means being located above the testicles. The loop means is attached to a slotted sheath of polymeric material which sheaths the penis in its normal or "rest" (non-erect) position; the sheath may be formed from an urine-absorbent ("u-a" for brevity) synthetic resinous material; or, the sheath may be formed from a natural fabric such as cotton, or a non-absorbent synthetic resinous material in which sheath a u-a liner means, preferably of polymeric material such as a carboxylic acid-containing polymer is removably held.

It is therefore a general object of this invention to provide a sheath of u-a material for a penis in its normal or "rest" position, which sheath is retained in position by a loop means adapted to be snugly but comfortably fitted under the upper portion of the scrotum, and optionally, over the base of the penis of the user; alternatively, to provide a u-a liner means for a sheath of non-absorbent or urine-impervious synthetic resinous material, which sheath is analogously retained in position.

It is a specific object of this invention to provide a longitudinally slotted, flat, thin-walled, tubular sheath and integral loop, each of predetermined size to be comfortably and effectively usable with the genitals of the user, the sheath and loop being formed from a flexible but essentially non-resilient and non-elastomeric material, the relative position of each being such as to allow the penis to be unsheathed through the slot before and after urination without dislodging the loop from around the scrotum because the loop is large enough to allow only one testicle at a time to be passed through the loop.

It is a particular object of this invention to provide an elongate, flat, thin-walled tubular sheath and loop means which can singly or combinedly be particularly chosen for comfort when used on the genitals of each individual user; and the sheath includes a u-a material to absorb a post-urinary drip.

It is also a particular object of this invention to provide a slotted sheath in which a longitudinal slot is provided over a major portion of the length of the sheath, preferably in the top thereof, to enable a sheathed penis to be quickly unsheathed for urinating by simply pulling the penis through the slot; and, to provide relief from constriction upon erection of the penis, by permitting egress of the penis through the slot in the upper portion.

BRIEF DESCRIPTION OF THE DRAWINGS

The foregoing and other objects and advantages of our invention will appear more fully from the following description, made in connection with the accompanying drawings of preferred embodiments of the invention, wherein like reference characters refer to the same or similar parts throughout the several views and in which:

FIG. 1 is a side elevational view diagrammatically illustrating a u-a sheath which is integrally formed with a loop retention means held in place by the upper portion of the base of the penis, the scrotum and testicles so as to retain the sheath on the penis, shown in phantom outline, in its normal or rest position.

FIG. 2 is a plan view of the u-a sheath of FIG. 1, including an outline illustrating the relative position of the loop around the testicles and the penis after it is sheathed.

FIG. 3 is a side elevational view showing the u-a sheath integrally attached to a loop means, the point of attachment being near the top of the sheath, at the open end of the sheath.

FIG. 4 is a plan view of the u-a sheath shown in FIG. 3 showing the relative position of the loop and the sheath which is slit longitudinally along its upper surface.

FIG. 5 is a plan view of a laminar blank of a u-a material from which the preferred embodiment of the device may be formed by securing opposed edges, except for those which form the slot.

DETAILED DESCRIPTION OF PREFERRED EMBODIMENTS

Figure 6:
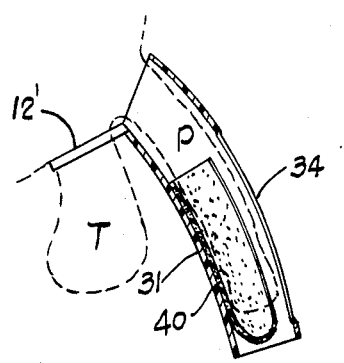
FIG. 6 is a side elevational view, partially in cross-section, showing a u-a liner removably inserted in a urine-impervious sheath integrally formed with a loop means, the point of attachment being near the bottom of the sheath at the open end thereof.

Referring now to the drawing, and more particularly to FIG. 1, there is shown a first preferred embodiment of a hygenic device, indicated generally by reference numeral 10 having a flexible unitary body construction with an elongated, thin-walled tubular portion, or sheath 11; and, a loop means 12 which integrally formed as part of the body of the device. The sheath 11 is closed at its one end 13. In the top of the sheath is provided a slot 14, shown in FIG. 4 as having been notched out longitudinally over a major portion of the length of the sheath.

The sheath is formed from a u-a, relatively high strength hydrophilic polymer film formed from a block-copolymer of sequences of acrylonitrile and sequences of a major portion of glutarimide units such as is disclosed in U.S. Pat. Nos. 4,331,783 and 4,369,294; or, a film formed from sequences of acrylonitrile and sequences of a major portion of acrylamide units as disclosed in U.S. Pat. No. 4,337,327; or, a film formed from a polymeric composition consisting essentially of polyacrylonitrile and a block copolymer with acrylonitrile and non-crystalline sequences such as is disclosed in U.S. Pat. Nos. 4,379,874 and 4,420,589 to Stoy, the disclosures of which are incorporated by reference thereto as if fully set forth herein.

The sheath 11 is essentially non-resilient and non-elastomeric, but flexible because it is made from self-supporting polymer (referred to herein as a "first" polymer for ease of identification) film having a thickness in the range from 1 mil to about 20 mil, more preferably from about 2 to 10 mils. The thickness of the film is not narrowly critical provided the sheath is flexible enough for comfort. Also, a relatively thin film of a desirable u-a polymer will "breathe" thus enhancing comfort.

It is most important that the sheath be able to absorb the post-urinary drip, and not disintegrate after being soaked, hence termed "relatively high strength". Homopolymers of acrylic acid or methacrylic acid (together referred to herin as "(meth)acrylonitrile") and alkali metal salts thereof, or copolymers of (meth)acrylic acid and esters thereof which homopolymers or copolymers disintegrate relatively easily when saturated with urine, are referred to herein as "relatively low strength" u-a polymers. Such relatively low strength ua polymers (referred to herein as "second" polymers) of carboxylic acid esters, and of carboxylic acids, are described in U.S. Pat. Nos. 2,798,053; 3,915,921; and 4,509,949 inter alia, the disclosures of which are incorporated by reference thereto as if fully set forth herein, some of which are commercially available under the Carbopol brand, may be used in conjunction with the first polymer from which the sheath is formed, as will be explained in detail hereinafter. It is essential that the u-a polymer, whether high or low strength, be able to absorb at least its weight in urine, and preferably from about 2 to about 100 times its weight when saturated. Typically, in use, the u-a polymer will absorb from about 0.1 ml to about 10 ml of urine dripped after a single urination.

The length of the sheath is desirably long enough to accomodate the normal length of a penis P in its "rest" position, and the diameter of the sheath is large enough so that neither the length nor the diameter unduly constricts the penis at rest. It will immediately be evident that it is most desirable to have a sheath having preselected dimensions to suit the user of the device.

The slot 14 in the top of the sheath is provided to allow the penis to be pulled out of its sheath without altogether removing the sheath, that is, so that the sheath remains pendant from the base of the penis during urination. Since the sheath is flexible it is generally sufficient only to slit the sheath. The slit terminates at one end about an inch from the closed end 13 of the sheath, and at the other end, about an inch from the open end 15 of the sheath, so that, in general the slot 14 will extend over a sufficient distance to allow the penis easily to be pulled from the sheath, then resheathed.

It is not critical that the slot be in the upper surface of the sheath, it being quite feasible to unsheath the penis through a slot in either side, or in the lower portion of the sheath (none of which alternative positions need specifically be illustrated), provided that the length and width of the slot be sufficient for the purpose of allowing egress.

In the most preferred embodiment, illustrated in the plan view shown in FIG. 4, the slot 14 extends over a major length of the sheath. This length of slot has the additional advantage that an erection of the penis will arch the organ through the slot and permit its easy egress, so that, if coitus is in the offing, the penis is freed from its sheath.

The loop means 12 is adapted to be fitted under the upper portion of the scrotum and serves only to hold the sheath on the penis. Because it is desirably formed from the same polymeric film as the sheath, the loop is also flexible. The diameter of the loop is so chosen as to be too small to permit both testicles T to be inserted simultaneously through the loop. Since the testicles function to anchor the loop above them, the loop is desirably just large enough to push one testicle at a time through it.

It will now be evident that, like the sheath 11 which has dimensions desirably preselected to function comfortably with the particular dimensions of the penis of the user, the loop 12 will also desirably have a diameter preselected to function with the particular dimensions of the testicles of the user.

It will now be evident that the dimensions of the sheath 11 are less critical to the function of the device than those of the loop 12 if the loop is essentially inextensible. It is the surprisingly effective functioning of a properly dimensioned loop of hydrophilic polymer which makes this device a successful beltless device. For example, with testicles having a nominal diameter of 1.0", an essentially inextensible loop having a diameter of about 1.5" will function adequately. It is preferred to provide such loops in a range of sizes, and sheaths in a range of sizes, so that a user can select the matching size of sheath and loop best adapted for his personal use.

It will be appreciated that the thin film of hydrophilic polymer forming the loop may be slightly extensible, but in general, an extension more than 25% greater than the original diameter will tear the loop. Slight extensibility provides for tolerance in selection of a loop for maximum comfort and effectiveness. An extensible loop may be used in another embodiment of this invention wherein the sheath and the loop are detachably secured to each other, as will be presently described hereinbelow.

As shown in FIG. 1, and more clearly in FIG. 3, the loop is integrally formed with the upper portion of the sheath, that is, near the periphery of the open end of the sheath which would be contiguous to the upper surface of the penis, and is referred to as the "upper peripheral attachment point". This arrangement provides for a larger loop which encircles both the penis and the scrotum above the testicles, so that the testicles may be easily inserted through the loop. Alternatively, the attachment point may be near the lower periphery of the open end 15 of the sheath ("lower peripheral attachment point"), and the loop dimensioned, as shown in FIG. 6, to just pass one testicle through at a time, as designated hereinabove.

Referring now to FIG. 5 there is shown a plan view of a cut-out of laminar polymer film, indicated generally by reference numeral 20. When the cut-out is folded symmetrically about its longitudinal axis, opposite edges 21 and 21', 22 and 22', and 23 and 23', are joined to form seams; edges 24 and 24' are left unsecured to provide the access and egress slot for the penis. The edges 21, 21' and 22, 22', and 23, 23' may be secured by any conventional means, as for example by heat sealing, or sealing with actinic radiation, the particular method used being chosen for the physical characteristics of the polymer used.

The loop 12 is formed by sealing opposed surfaces of the cut-out along one or more lines 25 and 26 (seen in FIG. 3). This is accomplished by sealing along dotted lines 25 and 25', and/or lines 26 and 26' as shown in FIG. 3. The particular means for sealing the opposed surfaces of the cut-out to form the loop is not critical provided sufficient strength is imparted to the loop to serve its function.

Referring to FIG. 6 there is diagrammatically illustrated a side elevational view showing a urine-impervious sheath 31 integrally formed with a loop means, the point of attachment being near the bottom of the sheath. The loop 12' is dimensioned to just allow a single testicle to be pushed through it, so that when both testicles are sequentially pushed through, the loop is snugly held by the upper portion of the scrotum, above the testicles, encircling them directly beneath the base of the penis, and securely holding the sheath in place after the penis is inserted into it. A strip 40 of u-a material is inserted in the sheath by folding it at right angle to its longitudinal axis, and pushing it into the sheath with a finger so that the strip lines the opposed sides of the sheath. The penis P is simply pulled out of the slot 34, and after urination is resheathed so that the post-urinary drip is absorbed by the strip.

Figure 7:
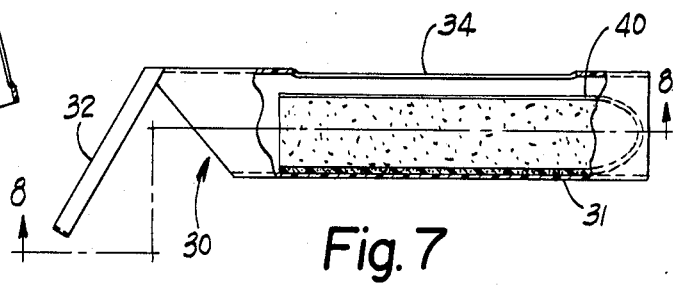
FIG. 7 is a side elevational view, partially in cross-section, of an urine-impervious sheath of thin self-supporting polymeric film, in which sheath a strip of u-a material is removably disposed so as to line the sheath.

Referring to FIG. 7 there is shown a side elevational view of a device 30, formed from a self-supporting urine-impervious polymer film. The urine-impervious polymer film may be of any suitable film-forming polymer including homopolymers and copolymers, and mixtures thereof, of poly(mono-1-olefins) such as high and low density polyethylene, polypropylene, etc., ethylenepropylene copolymers; polyurethanes such as are prepared from polyols and organic polyisocyanate; polyamides such as hexamethylene-adipamide; polyesters such as polymethyleneterephthalates; polyacrylics and the like. The sheath 31 is formed in an analogous manner to that described hereinabove in FIGS. 1–5, as is the slot 34 in the sheath, and the loop 32. As before, the loop 32 may optionally be provided with an upper or a lower attachment point. A mass of u-a material is placed in the sheath, this being conveniently accomplished with a strip 40, though the shape of the material is not critical, and may be arbitrary, the sole requirement being that the material be in contact with urine dripped into the sheath. A thin strip from about 1 cm to about 3 cm wide and 1 mil to about 50 mil thick is conveniently and easily inserted as a lining against the opposed interior walls of the sheath, hence referred to herein as a "linered sheath", and may just as easily be removed and discarded when it is soaked. Such u-a materials are typically copolymers and homopolymers of alkali metal salts of carboxylic acids and/or carboxylic acid esters such as are conventionally used for the purpose, namely absorbing body fluids, in sanitary napkins for women, and disposable diapers for children. A strip having a width less than the diameter of the sheath may be cut from a sheet of poly(acrylic acid salt) made as described in U.S. Pat. No. 4,466,993.

Figure 8:
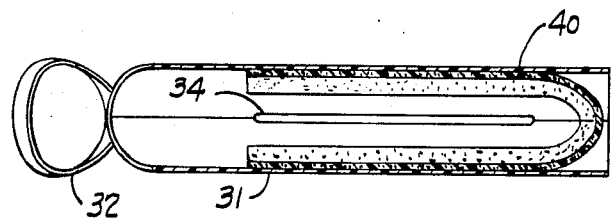
FIG. 8 is a bottom view, partially in cross-section, in longitudinal cross section along the line 8—8, of the device shown in FIG. 7.

FIG. 8 is a bottom view of the device shown in FIG. 7, shown as a cross sectional view along the line 8—8 in FIG. 7, showing how a strip lies along opposed side walls of the sheath, leaving the slot above accessible for egress of the penis. It will be appreciated that the post-urinary drip from the resheathed penis will drip into the closed end of the sheath and be absorbed by the liner. Since the sheath itself is preferably urine-impervious, any urine not immediately absorbed in the closed end of the sheath will subsequently be absorbed in the unsoaked position of the strip.

Figure 9:
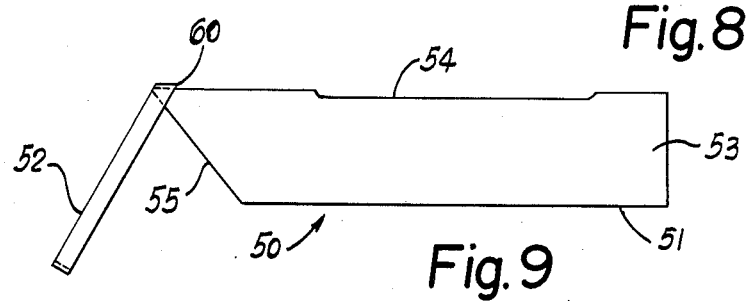
FIG. 9 is a side elevational view diagrammatically illustrating a detachably attached linerless u-a sheath and loop in a beltless device in an embodiment utilizing an upper attachment point.

Referring to FIG. 9 there is shown another embodiment of the invention in which the device 50 comprises a sheath 51 detachably attached to a loop retention means 52, for example, by means of an attachment means 60 such as for example cooperating small, about 1 cm×1 cm patches of Velcro interlocking polymer loops or "fingers" adhesively secured to the lower surface of the loop and the upper surface of the sheath, near the periphery of the open end thereof, in the upper attachment mode; or, secured to the upper surface of the loop and the lower surface of the sheath, near the periphery of the open end thereof, the point of attachment through the attachment means not being critical. As before, the sheath 51 is provided with a longtitudinal slot 54 in the upper surface, one end 53 is closed, and the other end 55 is open.

Figure 10:
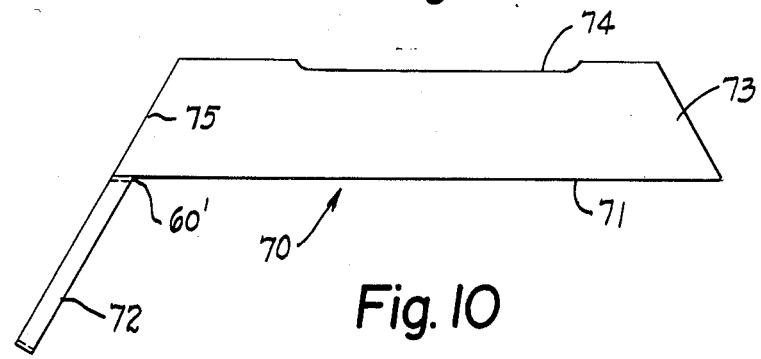
FIG. 10 is a side elevational view diagrammatically illustrating a detachably attached sheath and loop in a device in an embodiment utilizing a lower attachment point.

Referring to FIG. 10 there is shown still another embodiment of a device 70 in which the sheath 71 is detachably attached to a loop 72 at a lower attachment point, by Velcro attachment means 60'. As before, the sheath has one closed end 73, the other end 75 being open; and, a slot 74 is provided in the sheath. One of the cooperating Velcro pads 60' is preferably secured to the upper surface of the loop 72, and the other to the lower surface of the periphery of the sheath, near the open end 75 thereof.

The attachment means itself is not narrowly critical and may be a small patch of adhesive which is kept covered on each of the surfaces to be adhesively secured until ready for use, then bared. In this mode, the loop 52 may be formed from the same or different material from the sheath, each being selected by the user, for precise fit and maximum comfort.

Though the purpose of the linered sheath is best served when the sheath is made from an impervious synthetic resinous material, it may also be made from a natural polymer such as cotton which is pervious. The liner is effective to absorb the urine immediately, thus preventing the urine from permeating the pervious sheath. A cotton sheath may be attached to a cotton, linen or leather loop by means of cooperating snap-tab connections or the like affixed to each. The advantage of such separable natural polymeric materials is that they are washable and reusable after the soaked liner is discarded.

In another embodiment, also illustrated by FIG. 9, the separable sheath 51 may be a disposable u-a hydrophilic polymer, and the loop 52 may be of the same or different material, each provided with suitable attachment means adapted to detachably secure them, and again, the loop and sheath may be provided with either an upper or a lower attachment point. Thus, the sheath may be made from u-a hydrophilic polymer and the loop made of stretchable woven rubberized fabric such as is commonly used in the elastic waist bands of undershorts, suspenders and the like. Or, the sheath may be made from woven or non-woven synthetic or natural polymer fibers, and the elastic loop retained.

Whether an integrally formed sheath and loop is used, or whether they are separably attached, the device is most conveniently used by first inserting the penis into the sheath, then pushing each testicle individually through the loop. Where the sheath and loop are separable it may be equally convenient to push the testicles through the loop first to position it comfortably, then insert the penis into the sheath and secure it to the loop by the attachment means. Typically, a sheath of hydrophilic polymer is used for one day, then discarded.

We claim:

1. A disposable absorbent urinary sheath for post urinary drip comprising a single flat blank of essentially flexible non-resilient non-elastomeric polymer film having a thickness in the range of 1 to 20 mils, said blank having a longitudinal axis forming a line about which said blank is foldable to form a urinary sheath, said blank having two opposing longitudinal edges and two transverse edges, said transverse edges forming a closed end and an opposed end means having a loop means, said loop means secured longitudinally to said blank to provide means to support said sheath to the upper portion of the scrotum of a user, means on opposite longitudinal edges to provide longitudinal open slot means to provide access and egress of a penis after said blank is formed.

2. The blank of claim 1 wherein said material is an urine-absorbent polymer having sufficient strength to maintain the integrity of the sheath until it is disposed of.

3. The blank of claim 2 wherein said urine-absorbent polymer is selected from the group consisting of a block copolymer of sequences of acrylonitrile and sequences of a major portion of glutarimide units; sequences of acrylonitrile and sequences of a major portion of acrylamide; and, a polymeric composition consisting essentially of polyacrylonitrile and a block copolymer with acrylonitrile and non-crystalline sequences.

* * * * *